(12) United States Patent
Rastegar et al.

(10) Patent No.: US 6,770,024 B1
(45) Date of Patent: Aug. 3, 2004

(54) IMPLANTABLE COUNTERPULSATION CARDIAC ASSIST DEVICE

(75) Inventors: Jahangir S. Rastegar, New York City, NY (US); Harry Soroff, New York City, NY (US)

(73) Assignee: Stony Brook Surgical Innovations, Inc., Northport, NY (US)

( * ) Notice: Subject to any disclaimer, the term of this patent is extended or adjusted under 35 U.S.C. 154(b) by 0 days.

(21) Appl. No.: 09/536,789

(22) Filed: Mar. 28, 2000

(51) Int. Cl.$^7$ .............................................. A61B 1/362
(52) U.S. Cl. ..................... 600/16; 623/3.11; 623/3.16; 623/3.21
(58) Field of Search ................ 600/16, 17; 623/3.1, 623/3.11, 3.16, 3.21, 3.22, 3.28

(56) References Cited

U.S. PATENT DOCUMENTS

| | | |
|---|---|---|
| 3,656,873 A | 4/1972 | Schiff |
| 3,685,059 A | 8/1972 | Bokros et al. |
| 3,700,380 A | 10/1972 | Kitrilakis |
| 3,911,897 A | 10/1975 | Leachman, Jr. |

(List continued on next page.)

*Primary Examiner*—Angela D. Sykes
*Assistant Examiner*—Roderick Bradford
(74) *Attorney, Agent, or Firm*—Frommer Lawrence & Haug LLP; Dennis M. Smid

(57) ABSTRACT

A hollow tubular element is inserted in the descending aorta. The caudad end contains a pressure sensitive passive or preferably, hydraulically or electrically activated, unidirectional valve. A flexible diaphragm situated in a rigid shell affixed over an opening in the element wall divides the shell interior into first and second variable volume chambers. The first chamber opens to the artery. A continuously operating electrical pump is connected to the second chamber through a closed hydraulic system including a multi-valve chamber. The valves regulate fluid flow to the second chamber in accordance with electrical signals from the heart. Fluid flow is directed to the second chamber during cardiac diastole and away from the second chamber during cardiac systole, causing the device to function in a counterpulsation mode. The work of the heart is decreased and coronary blood flow is increased to promote the formation of new coronary collateral channels and the perfusion of the heart itself. In the event of mechanical failure, pre-implantation heart function is not impeded.

13 Claims, 4 Drawing Sheets

U.S. PATENT DOCUMENTS

| | | |
|---|---|---|
| 4,016,871 A | 4/1977 | Schiff |
| 4,172,295 A | 10/1979 | Batten |
| 4,173,796 A | 11/1979 | Jarvik |
| 4,175,264 A | 11/1979 | Schiff |
| 4,231,354 A | 11/1980 | Kurtz et al. |
| 4,302,854 A | 12/1981 | Runge |
| 4,364,127 A | 12/1982 | Pierce et al. |
| 4,378,435 A | 3/1983 | Takagi et al. |
| 4,583,523 A | 4/1986 | Kleinke et al. |
| 4,685,446 A | 8/1987 | Choy |
| 4,731,076 A | 3/1988 | Noon et al. |
| 4,771,765 A | 9/1988 | Choy et al. |
| 4,822,357 A | 4/1989 | Forster et al. |
| 4,902,273 A | 2/1990 | Choy et al. |
| 5,006,104 A | 4/1991 | Smith et al. |
| 5,131,905 A | 7/1992 | Grooters |
| 5,133,744 A * | 7/1992 | Ramos Martinez ........ 623/3.21 |
| 5,139,020 A | 8/1992 | Koestner et al. |
| 5,171,207 A | 12/1992 | Whalen |
| 5,258,023 A | 11/1993 | Reger |
| 5,269,811 A * | 12/1993 | Hayes ........................... 623/3 |
| 5,282,850 A | 2/1994 | Davidson |
| 5,346,458 A | 9/1994 | Affeld |
| 5,360,445 A | 11/1994 | Goldowsky |
| 5,377,671 A | 1/1995 | Biondi et al. |
| 5,469,868 A | 11/1995 | Reger |
| 5,502,216 A | 3/1996 | Mori et al. |
| 5,511,958 A | 4/1996 | Chen et al. |
| 5,599,173 A | 2/1997 | Chen et al. |
| 5,653,676 A * | 8/1997 | Buck et al. ................... 600/16 |
| 5,674,281 A | 10/1997 | Snyder |
| 5,722,429 A | 3/1998 | Larson, Jr. et al. |
| 5,758,666 A | 6/1998 | Larson, Jr. et al. |
| 5,810,708 A | 9/1998 | Woodard et al. |
| 5,843,129 A | 12/1998 | Larson, Jr. et al. |
| 5,848,962 A | 12/1998 | Feindt et al. |
| 5,861,010 A | 1/1999 | Boussignac et al. |
| 6,007,479 A * | 12/1999 | Rottenberg et al. ........... 600/16 |
| 6,030,335 A * | 2/2000 | Franchi ....................... 600/16 |

\* cited by examiner

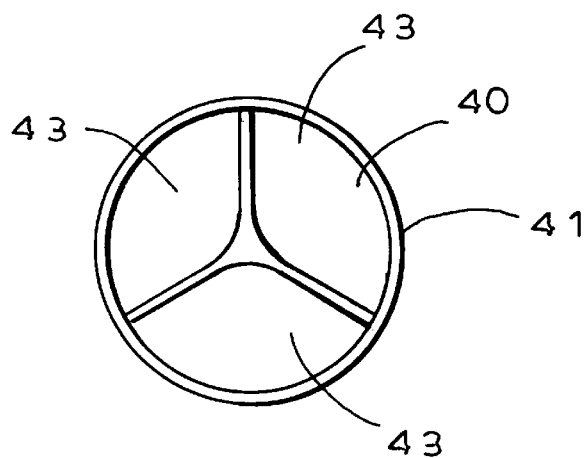
FIG. 4
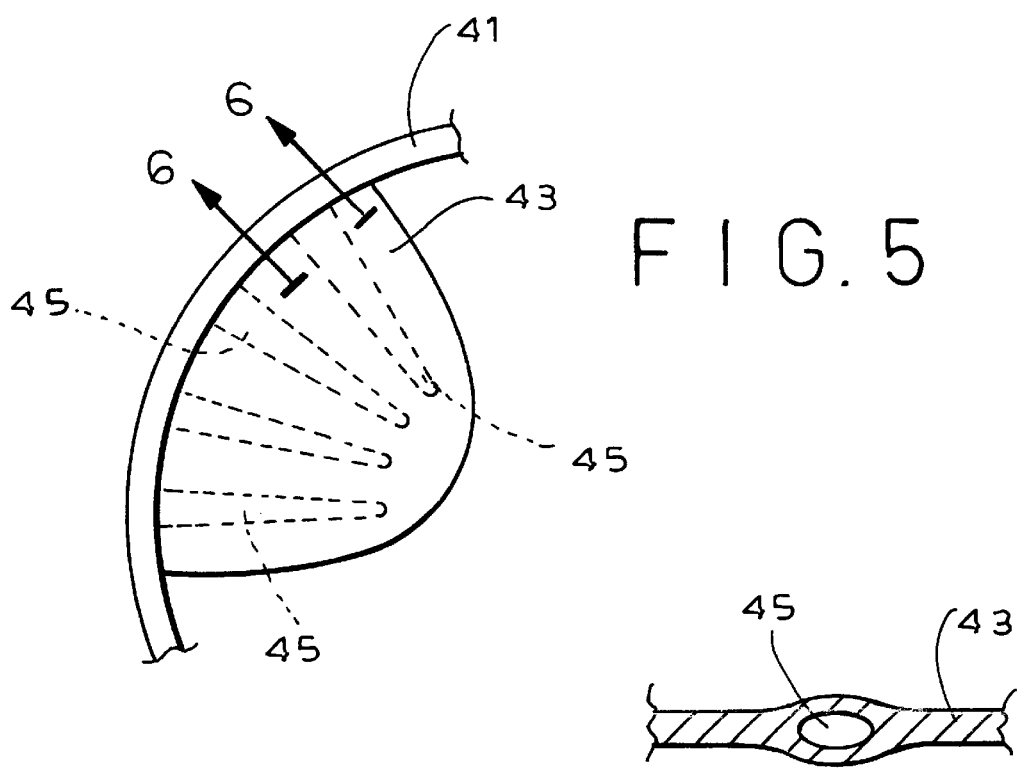
FIG. 5
FIG. 6

IMPLANTABLE COUNTERPULSATION CARDIAC ASSIST DEVICE

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to a cardiac assist device and more particularly to an implantable artificial left ventricle including a continuously operating pump and hydraulic valve system which assists the heart by intermittently pumping blood in synchronization with operation of the heart.

Congestive heart failure represents an enormous national public health concern, with,a prevalence of 4.9 million cases and an incidence of more than 400,000 cases a year. Some 50,000 people a year die of heart failure and it is a contributing factor in 250,000 additional deaths a year.

Congestive heart failure accounts for more than 800,000 hospitalizations a year, at a hospital cost of $18.8 billion. The direct and indirect cost of treating this disease has been estimated at $64 billion a year.

Congestive heart failure is the only form of heart disease that is increasing in the United States. It will undoubtedly continue to do so, as more and more victims of coronary occlusions survive and their longevity is increased. However, with each such event, the heart muscle is further injured and the resulting scar tissue decreases the ability of the left ventricle to perfuse the body. Thus, higher survival rates and increased longevity lead to an increased number of people surviving long enough for congestive heart failure to become a likelihood. The development of a device to augment or replace the pumping ability of the left ventricle would prevent congestive heart failure.

(2) Description of Related Art Including Information Disclosed Under 37 CFR 1.97 and 1.98

During the last twenty years, a variety of mechanical devices have been developed to support circulation. These devices, known as ventricular assist devices, usually aimed at the left ventricle, (sometimes known as LVAD's) have been used primarily for temporary short-term-circulatory support as a bridge to cardiac transplantation. The success of these devices has led to the understanding that LVAD's may well be developed as a long-term therapy for patients with end-stage heart disease. Further, the utilization of LVAD's for patients with chronic heart disease has been recognized as a permanent treatment option for many patients.

The existing implantable cardiac assist ventricles either modify the anatomy of the heart (apico-aortic assist), replace the heart entirely, or use an atrial to aortic pump which provides a constant blood flow.

The present invention takes a different approach. It is essentially an implantable artificial ventricle that leaves the heart intact, improves the function and nutrition of the cardiac muscle, and normalizes the perfusion of the entire vascular system. Our device is designed such that in the event of mechanical failure, it will not impede pre-implantation operation of the heart. Hence, the patient is not medically worse off than he would have been without the device, if it were to fail.

The present invention utilizes a counterpulsation pumping action and a unique valve structure. The device pumps blood during each cardiac diastole but not during cardiac systole. The result is that the work of the heart is decreased during systole. Coronary blood flow and perfusion of the heart itself are increased during cardiac diastole, when the transmural cardiac resistance is at its nadir. The increased coronary flow during cardiac diastole has an angiogenic effect, i.e., it promotes the formation of new coronary collateral channels. This beneficial effect has been shown to be associated with an improvement in left ventricular function, and a significant decrease in angina.

Our invention provides for long term implantation of a counterpulsating chamber in the descending aorta, either above the diaphragm or below the inferior mesenteric artery, which will assist the failing or failed left ventricle. Candidates for such an assist system would, at first, be NYHA Grade IV patients, in chronic failure and bedridden. As the procedure gains acceptance, it would be implanted in somewhat less severely ill patients.

We utilize a closed hydraulic fluid system which includes a hydraulic pump. The pump has a continuously operating voice coil linear electric motor which drives a hydraulic piston. The motor and piston are preferably constructed as a single sealed unit, with the motor submersed in hydraulic oil, so as to be supported on its own hydrodynamic oil bearing. Such a pump is disclosed in detail in U.S. Pat. No. 5,360,445, entitled "Blood Pump Actuator," issued to Goldowsky on Nov. 1, 1994.

As indicated in the Goldowsky patent, this arrangement greatly increases the life of the pump by eliminating wear at the bearings. The hydraulic fluid is selected to have a very low viscosity and very good lubrication capability.

Hydraulic valves are utilized to convert the continuous fluid flow output of the pump into the intermittent fluid flow needed to provide the desired counterpulsed blood flow. The valves are controlled in accordance with electrical signals from the heart such that blood is pumped only during cardiac diastole.

The valves are situated in a multi-valve body or chamber. After closure of the aortic valve, hydraulic fluid is pumped into a variable volume chamber which expands, causing blood to be forced into the arteries. During the next cardiac systole, fluid is pumped from the chamber, into a fluid reservoir which accumulates the fluid during pump diastole, such that no force is exerted by the device on the circulatory system.

A bypass is employed to relieve the fluid build-up in the chamber, if the pressure rises above a given level. This might take place, for instance, if a pause occurs in the operation of the valves due to a pause in the rhythm of the heart. The bypass permits the pump to continue to operate without overloading the closed hydraulic system.

It is therefore a prime object of the present invention to provide an implantable cardiac assist device which operates in a counterpulsation mode.

It is therefore another object of the present invention to provide an implantable counterpulsation cardiac assist device which utilizes a continuously operating hydraulic pump in a closed hydraulic system.

It is still another object of the present invention to provide an implantable counterpulsation cardiac assist device with hydraulic valves regulated in accordance with heart operation.

It is still another object of the present invention to provide an implantable counterpulsation cardiac assist device which includes a tubular element adapted to be implanted in the aorta and having a variable volume hydraulic chamber.

It is still another object of the present invention to provide an implantable counterpulsation cardiac assist device where the caudad end of the tubular element includes a unidirectional pressure sensitive valve.

It is still another object of the present invention to provide an implantable counterpulsation cardiac assist device which increases coronary blood flow.

It is still another object of the present invention to provide an implantable counterpulsation cardiac assist device which promotes the formation of new coronary collateral channels.

It is still another object of the present invention to provide an implantable counterpulsation cardiac assist device which promotes perfusion of the heart.

It is still another object of the present invention to provide an implantable counterpulsation cardiac assist device which, in the event of mechanical failure, does not impede the operation of the heart.

BRIEF SUMMARY OF THE INVENTION

In accordance with one aspect of the present invention, an implantable cardiac assist device is provided, adapted to be inserted in an artery. The interior of the device is divided into first and second variable volume chambers. The first chamber is connected to the artery. A continuously operating pump is hydraulically connected to the second chamber by valves means which regulate fluid flow to the second chamber in response to the operation of the heart, for directing fluid flow to the second chamber during cardiac diastole and away from the second chamber during cardiac systole.

The device includes a generally tubular element. A unidirectional pressure sensitive blood flow valve is situated proximate one end of the tubular element.

The device also includes a rigid shell. The shell is attached to tubular element, over an opening in the element wall. A flexible diaphragm is situated within the shell and divides the interior into separate chambers.

Control means for the valve means are provided. The control means includes means for monitoring the operation of the heart and for actuating the valves to regulate fluid flow to the second chamber in accordance with same. Monitoring means may be an electrocardiograph and, if present, a cardiac pacemaker as well.

The pump has a fluid inlet and a fluid outlet which are connected to a closed hydraulic system. The system includes a fluid reservoir to retain hydraulic fluid. The valves connect the pump outlet to the reservoir during cardiac systole. The valves connect the pump inlet to the second chamber during cardiac systole.

The system further includes a bypass conduit for connecting the pump output and the pump input. A bypass valve is situated in the bypass conduit.

The artery into which the element is inserted is preferably the descending aorta. The element is placed in the descending aorta between the coronary arteries and heart, on the one hand, and the femoral and Iliac arteries, on the other hand.

An electric motor forms a part of the pump. transcutaneous energy transmitter is utilized to provide energy to the motor.

An electrocardiograph is provided for monitoring the operation of the heart. Means are provided for connecting the electrocardiograph to the valve control means.

In accordance with another aspect of the present invention, an implantable cardiac assist device is provided comprising a tubular element adapted to be situated in the descending aorta. A unidirectional pressure sensitive valve is situated in the end of the element facing away from the heart. First and second variable volume chambers are provided within a shell which is associated with the element. The first chamber is connected to the artery. A continuously operating pump, having an inlet and an outlet, is connected to a closed hydraulic system, including a fluid reservoir. Valve means, responsive to the operation of the heart, are provided for connecting the pump outlet to the second chamber, and the reservoir to the pump inlet, when the heart is in diastole. The valve means connects the pump outlet to the reservoir, and the second chamber to the pump inlet, when the heart is in systole. Bypass means are provided for connecting the pump outlet and the pump inlet.

The operation of the pressure sensitive valve is preferably synchronized with the valve means. In one embodiment, an electrically activated valve is utilized and is controlled by the valve means controller. In a second embodiment, a hydraulically actuated valve is utilized. In the latter case, the valve control input is connected by a conduit to the second chamber.

BRIEF DESCRIPTION OF THE SEVERAL VIEWS OF THE DRAWING(S)

To these and such other objects which may hereinafter appear, the present invention relates to an implantable counterpulsation cardiac assist device, as described in the following specification and recited in the annexed claims, taken together with the accompanying drawings, in which like numerals refer to like parts, and in which:

FIG. 4 is an elevation plan view of the mouth of the pressure sensitive valve;

FIG. 5 is a plan view of the side of the valve of FIG. 4; and

FIG. 6 is a cross-sectional view taken along line 6—6 of FIG. 5.

DETAILED DESCRIPTION OF THE INVENTION

Figure 1:
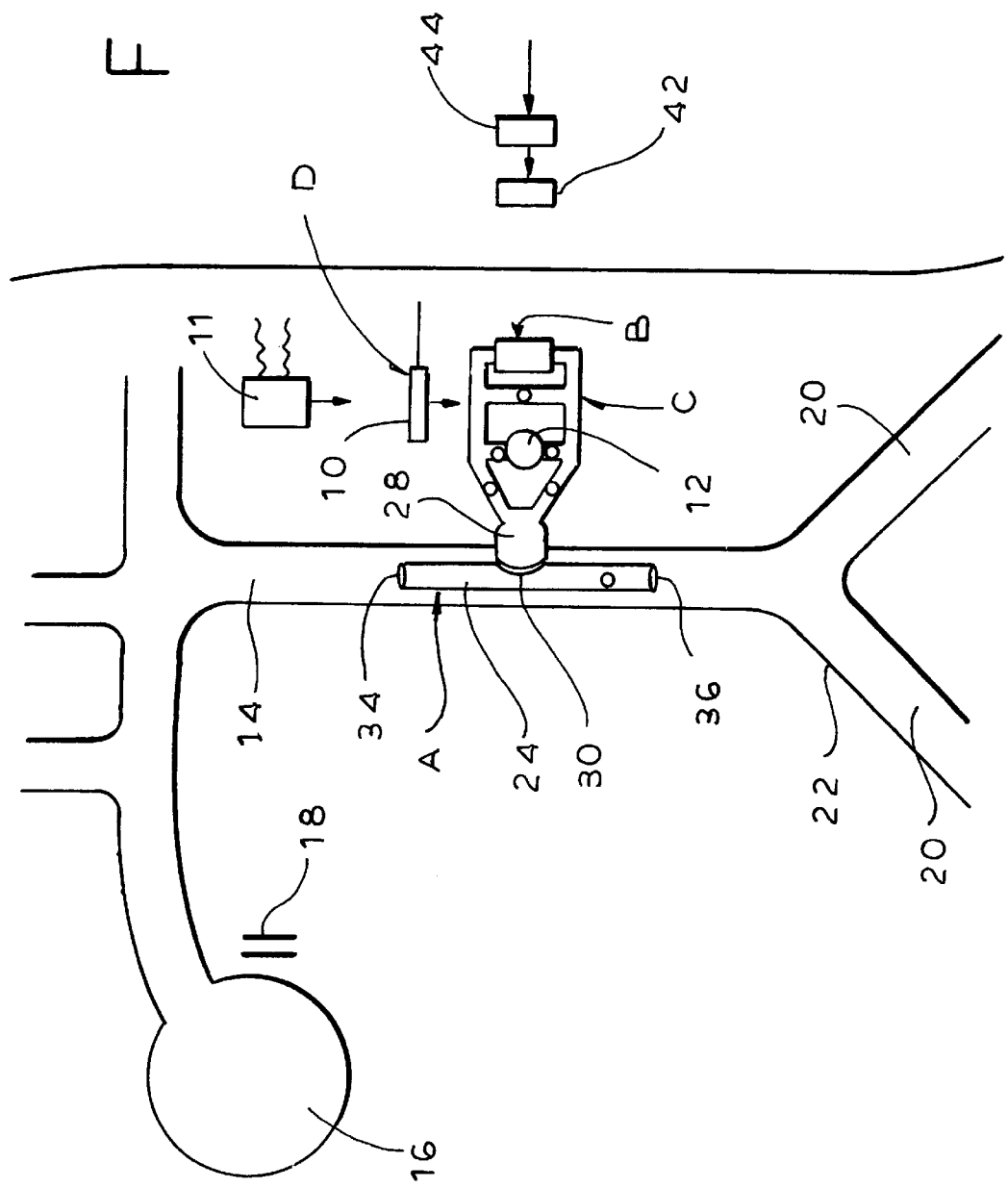
FIG. 1 is an idealized drawing of the human anatomy showing the location at which the device of the present invention is implanted.

As seen in FIG. 1, the implantable counterpulsation cardiac assist device of the present invention includes a hollow tubular element with a unidirectional pressure sensitive valve, and separate variable volume chambers, generally designated A, a sealed hydraulic pump unit, generally designated B, a closed hydraulic system including a multivalve chamber, generally designated C, which operably connects element A and pump B, and valve control means, generally designated D, which controls the valves in chamber C in a way that converts the fluid flow from continuously operating pump B to intermittently pump blood, in a counterpulsation mode, in synchronization with the operation of heart.

Valve controller 10 receives electrical output signals from an electrocardiograph (not shown) and controls the valves within chamber C in accordance with those signals. The electrocardiac signals are a function of the operation of the heart. Controller 10 may also receive output signals from a pacemaker 11, if present.

Chamber C includes a flexible walled fluid reservoir 12. Reservoir 12 expands as it collects hydraulic fluid during cardiac systole and collapses as hydraulic fluid is withdrawn during cardiac diastole, enabling pump B to operate continuously, while the device itself pumps blood intermittently.

The device is placed in the descending aorta 14, preferably between the left ventricle 16 and coronary arteries 18, on the one hand, and the femoral and Iliac arteries 20, on the other hand. It includes a tubular element 24 which is inserted into the artery via an incision. The most preferable location would be in the abdominal aorta below the inferior mesenteric artery, shown as area 22 on FIG. 1.

Tubular element 24 has an opening 26 in its side wall. A rigid shell 28 is attached to the side wall, over opening 26. A sewing ring 30 is used. It is stitched to the edges of the aorta, sealing element 24 in the artery. The shell contains a diaphragm 32 made of flexible bio-compatible material which is attached along the periphery of the shell and divides the shell into two variable volume chambers 33 and 35. Chamber 33 opens to the interior of the artery. As chamber 35 expands, the volume of chamber 33 decreases and blood is forced from chamber 33 and out the ends of element 24.

Figure 2:
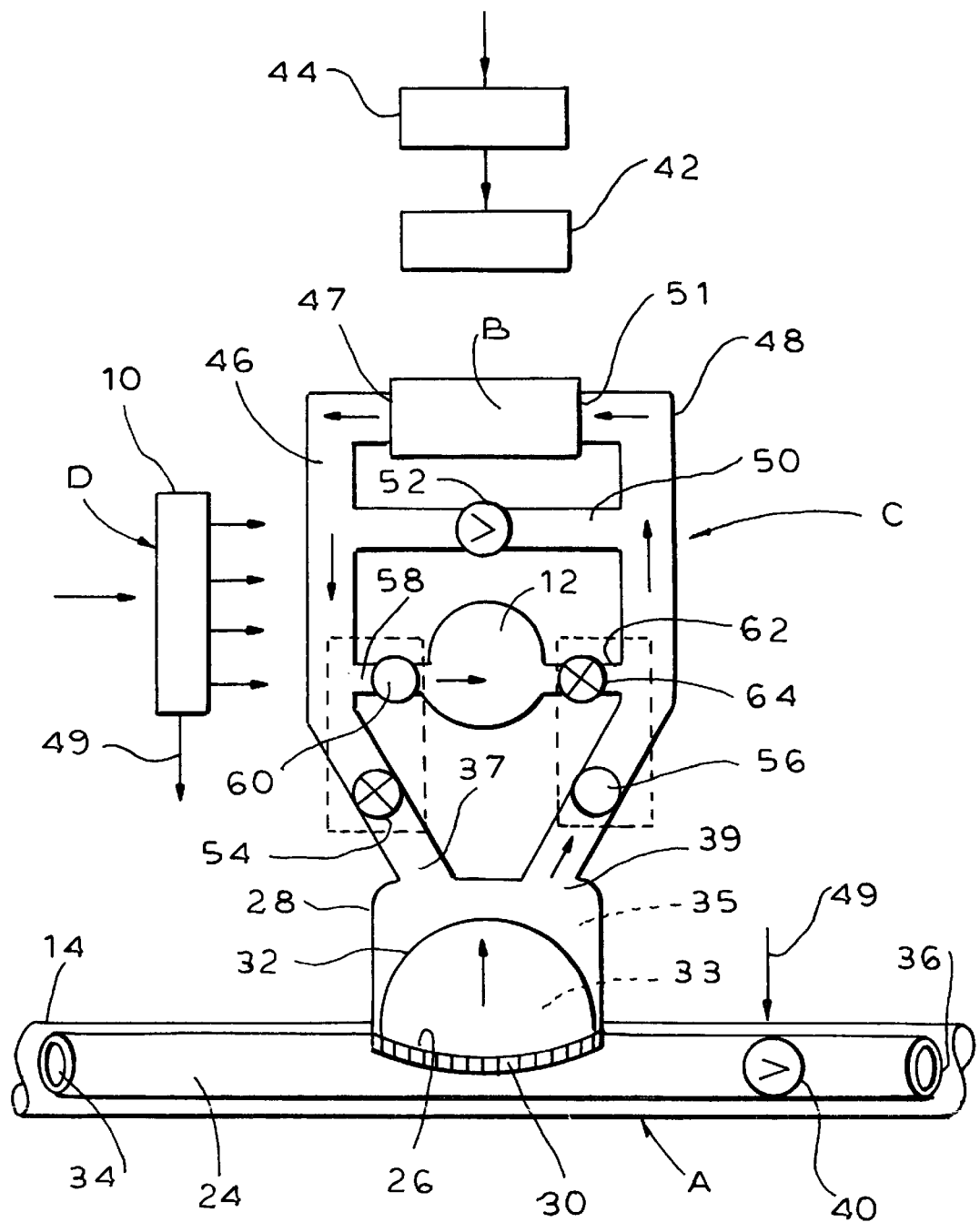
FIG. 2 is a schematic drawing of the device, showing the valve state during cardiac systole.
Figure 3:
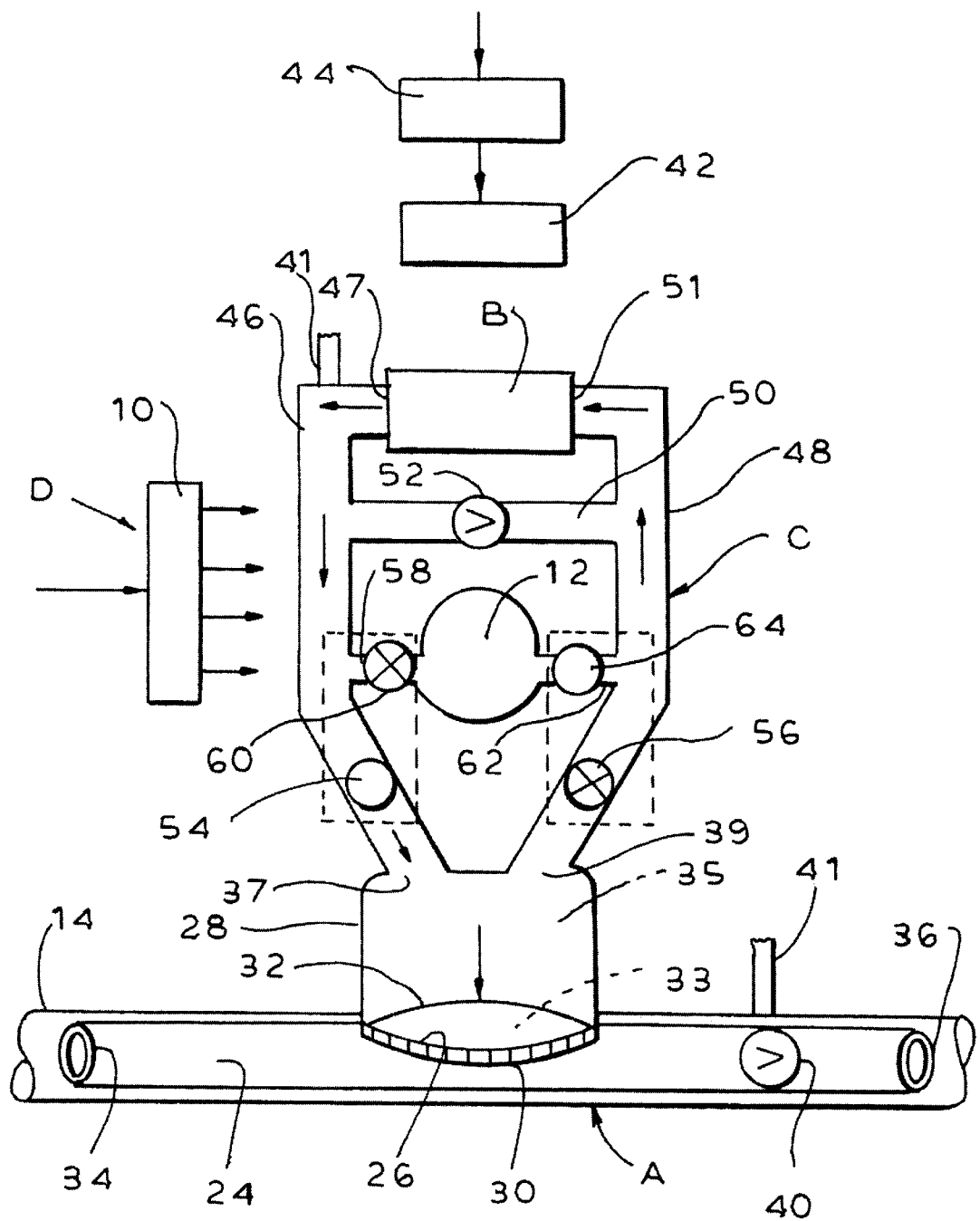
FIG. 3 is a schematic drawing of the device similar to FIG. 2, showing the valve state during cardiac diastole.

Tubular element 24 has its upper (cephalad) end 34 (left as seen in FIGS. 2 and 3) directed toward the heart and its lower (caudad) end 36 (right as seen in FIGS. 2 and 3) directed toward the Iliac arteries and the lower extremities. The pressure sensitive valve 40 is located proximate the caudad end of element 24. Valve 40 is a unidirectional pressure sensitive valve which both prevents back-flow from the lower extremities when the volume of chamber 35 is decreasing and regulates the direction of blood flow from the ends of the element when the volume of chamber 35 is increasing.

Valve 40 may be a passive valve designed so that it resists forward blood flow until a pressure threshold of about 90–100 mm.Hg is reached, during the systolic phase of the device. The resistance built into the valve 40 favors flow through the cephalad end 34 of element 24, towards the coronary arteries 18. The resultant increase in coronary blood flow creates the physical conditions which aid in the development of coronary collateral channels.

Passive versions of valves suitable for use in this application are available prosthetic aortic trileaflet valves, such as those disclosed in U.S. Pat. Nos. 5,258,023, 4,473,423, 5,469,868, 5,502,216, 4,364,127 and 4,172,295. The top view of such a trileaflet valve is shown in FIG. 4.

These valves generally have rigid frames 41 and flexible leaflets 43 attached to the frame. The leaflets 43 are arranged such that in the closed position, each leaflet contacts the adjacent leaflets, thereby closing the valve and preventing the flow of blood. In the open position, the leaflets separate from each other, radially opening out towards the inner walls of the artery. Leaflets 43 are preferably made out of bio-compatible plastic material with the required flexibility, such as polyurethane. The leaflets must be capable of withstanding the back pressure across the valve while in the closed position.

In the passive version of the valve, the leaflets are constructed with appropriate stiffness such that the valve stays essentially closed to the blood flow until the desired threshold pressure level is reached. The stiffness may be provided by various means such as metal spring inserts within the leaflets, rib type of leaflet stiffeners, by thickening part or entire leaflet section, or other similar means commonly used in similar components.

In the active versions, the leaflets are constructed such that they provide minimal resistance to the flow with minimal rise in the pressure across the valve, similar to the disclosed valves in the aforementioned patents. In these versions, the required stiffness of the leaflets is achieved by a mechanism activated hydraulically, electrically or with other similar means. The purpose of the activation mechanism is to stiffen the leaflets to the same level as in the passive version, i.e., to provide the stiffness necessary to resist flow until the desired threshold pressure level is reached.

Preferably a hydraulically controlled valve is used. In one embodiment, the leaflets 43 are constructed with one or more radically positioned channels 45 as shown in FIGS. 5 and 6. The channels are preferably connected to the chamber 35 by a conduit 41 (FIG. 3). During the operation of the cardiac assist device, the valve 40 is activated by hydraulic fluid flowing from conduit 41 into the leaflet channels 45, thereby so as to stiffen the leaflets to the desired level, at the desired stage of the operation of the assist device, i.e., during the initial stages of cardiac diastole. During the cardiac systole, the hydraulic fluid is pumped out of the leaflet cavities, thereby ensuring that the valve provides minimal resistance to blood flow. The resistance to the flow of blood will obviously be also minimized in case of failure of the assist device, i.e., if the hydraulic pump is either inoperational or cannot provide enough flow or pressure to properly operate the cardiac assist device.

Electrically controlled versions of such valves operate on a similar principle. During cardiac diastole, the valve receives an electrical activation signal via an electrical connection or cable 49 (FIG. 2) from controller 10 that causes the leaflets to stiffen. The signal is terminated during cardiac systole or in the case of cardiac device failure, thereby ensuring that the valve provides minimal resistance to the flow.

In the electrically controlled version of valve 40, the leaflets have similar radial channels as shown in FIG. 5, and are filled with an electrically (electrorestrictive fluid) or magnetically (magnetorestrictive fluid) activated fluid and sealed. The fluid channels are provided with the required electrically powered activation mechanisms. For the case of electrorestrictive fluids, conductive wires are placed within each fluid channel. A conductive coil would energize the magnetorestrictive fluid filled cavities.

Even though the leaflet channels were described to be filled with electrorestrictive or magnetorestrictive fluids, other activation materials such as electrically activated polymers may also be employed to provide similar stiffening of the leaflets upon electrical command.

Pump unit B preferably consists of voice coil linear electric motor which powers a hydraulic piston. The motor is a brushless DC motor that directly drives the piston. The electric motor and piston are constructed as a single, sealed pump unit. The motor is preferably submersed in hydraulic fluid and supported on its own hydrodynamic oil bearing, as disclosed in U.S. Pat. No. 5,360,445. This arrangement greatly increases the life of the pump by eliminating wear at the bearings. The hydraulic fluid will have a very low viscosity and very good lubrication capability.

The motor may obtain energy directly from a transcutaneous energy transmitter 42 located outside the body. Transmitter 42 is connected to a power pack 44 which, in turn, is connected to a power source, such as an electrical outlet, or one or more batteries. A rechargeable battery (not shown) may be implanted within the body and be connected to the motor, if desired.

As best seen in FIGS. 2 and 3, the closed hydraulic system includes conduit 46, one end of which is connected to pump outlet 47, a conduit 48, one end of which is connected to pump inlet 51 and a bypass conduit 50 connecting conduit 46 and conduit 48. A passive pressure sensitive bypass valve 52 is situated within bypass conduit 50 and serves to "short circuit" the system (that is, connect the pump outlet 47 directly to pump inlet 51) in the event that the pressure differential between conduits 46 and 48 rises above a predetermined level.

The other end of conduit 46 is connected to the inlet port 37 of chamber 35. A electrically controlled valve 54 is located in conduit 46, proximate chamber inlet port 37.

The other end of conduit 48 is connected to the outlet port 39 of chamber 35. An electrically controlled valve 56 is situated in conduit 48, proximate outlet port 39.

A conduit 58 connects conduit 46 and reservoir 12. An electrically controlled valve 60 is located in conduit 58. Reservoir 12 is also connected to conduit 48 by a conduit 62. An electrically controlled valve 64 is located in conduit 62.

Valves 54 and 60 may be configured as a single unit, including an electrically controlled valve with two outlet ports, one of which is open while the other is closed. The same may be true of valves 56 and 64. Alternatively, valves 54, 60, 56 and 62 may be configured as a single unit, including two, electrically controlled, dual position valves.

The operation of device A is illustrated in FIGS. 2 and 3. When the "R" wave in the ECG signal is detected by valve controller 10, signalling cardiac systole, controller 10 generates control signals which cause valves 54 and 64 to close and valves 56 and 60 to open. Hydraulic fluid is pumped through conduit 46 and conduit 58 into reservoir 12, causing reservoir 12 to expand. At the same time, fluid moves from chamber 35, through conduit 48 and into the pump inlet. This causes chamber 35 to decrease in volume, as is illustrated in FIG. 2.

When cardiac diastole is detected, controller 10 generates control signals to cause valves 54 and 64 to open and valves 56 and 60 to close, and if valve 40 is electrically activated, to cause valve 40 to resist blood flow for a short time interval. Fluid is pumped through conduit 48 into chamber 35, increasing the volume of chamber 35. This causes diaphragm 32 to move toward tubular element 24. Valve 40 will resist blood flow for a short time interval, if it is hydraulically activated. The rapidly decreasing volume of chamber 33 forces blood towards the heart and, after the delay due to the resistance of valve 40, toward the Iliac arteries. In the meantime, fluid from reservoir 12 flows out of the reservoir through conduit 62, into conduit 48 and thus to the pump inlet 51, thereby decreasing the size of the reservoir. This is illustrated in FIG. 3.

Conduits 46 and 48 are connected by bypass valve 52 which opens if the pressure differential in the conduits rises above a predetermined level. If there should be a pause in the operation of the device due to a pause in the rhythm of the patient's heart, the presence of the bypass valve permits continuous function of the pump without damaging any of the components of the device. However, if a pacemaker is present, the output of the pacemaker may provide an input to controller 10 to enable the device to continue operating even in the event of a pause in heart rhythm.

It should now be appreciated that the present invention is an implantable cardiac device which operates in the counterpulsation mode and utilizes a unidirectional pressure sensitive blood flow valve. The device functions to decrease the work of the heart and increase blood flow to the coronary arteries, as well as to the heart itself, during cardiac diastole. It utilizes a continuously operating pump and a closed hydraulic system with valves controlled in accordance with the operation of the heart.

While only a limited number of preferred embodiments of the present invention have been disclosed herein for purposes of illustration, it is obvious that many variations and modifications could be made thereto. It is intended to cover all of those variations and modifications, which fall within the scope of the present invention, as defined by the following claims:

We claim:

1. An implant able cardiac assist device comprising an enclosure having a flexible diaphragm and being adapted to be directly connected to an artery of a patient, means for receiving an indication regarding the operation of a heart of said patient, and a device coupled to said enclosure and operable to direct fluid flow to said enclosure to increase the volume of a portion of said enclosure during cardiac diastole and to direct fluid flow away from said enclosure to decrease the volume of said portion of said enclosure during cardiac systole.

2. The device of claim 1 wherein said the receiving means receives said indication from an electrocardiogram.

3. The device of claim 1 wherein said the receiving means receives said indication from a cardiac pacemaker.

4. The device of claim 1 wherein said device includes a continuously operating electric motor, a hydraulic pump and means for drivingly connecting said motor to said hydraulic pump.

5. The device of claim 1 wherein said device includes a pump and further comprising valve means operably connected between said pump and said enclosure.

6. The device of claim 1 wherein said device includes a pump and wherein said pump has an inlet and an outlet and further comprising a bypass conduit operably connecting said pump outlet with said pump inlet.

7. The device of claim 6 further comprising a bypass valve situated within said bypass conduit.

8. The device of claim 7 wherein said bypass valve is pressure sensitive.

9. The device according to claim 1 further comprising a unidirectional pressure sensitive blood flow direction control valve, said blood flow direction control valve providing minimal resistance to blood flow in a direction away from the heart during cardiac systole and providing maximum resistance to blood flow in the direction away from the heart during cardiac diastole.

10. The device according to claim 9 further comprising a tubular element adapted to be inserted within an artery.

11. The device of claim 10 wherein said blood flow control valve provides maximum resistance to blood flow through said caudad end of said tubular element until a specified pressure threshold is reached.

12. The device of claim 10 wherein said tubular element has a wall with an opening and further comprising means for connecting said enclosure to said opening in said wall.

13. The device of claim 10 wherein said tubular element is adapted to be placed in the descending aorta between the coronary arteries and the heart, on the one hand, and the femoral arteries, on the other hand.

* * * * *

UNITED STATES PATENT AND TRADEMARK OFFICE
CERTIFICATE OF CORRECTION

PATENT NO.    : 6,770,024 B1
DATED         : August 3, 2004
INVENTOR(S)   : Rastegar et al.

It is certified that error appears in the above-identified patent and that said Letters Patent is hereby corrected as shown below:

<u>Title page,</u>
Item [73], Assignee, change "Stony Brook Surgical Innovations, Inc., Northport, NY (US)" to -- PPTT LLC, 120 Harbor Road, Sands Point, NY (US) --

Signed and Sealed this

Twenty-eighth Day of December, 2004

JON W. DUDAS
*Director of the United States Patent and Trademark Office*